United States Patent
Dalkara et al.

(10) Patent No.: US 9,758,490 B2
(45) Date of Patent: Sep. 12, 2017

(54) ANTIFUNGAL COMPOUNDS OF (ARYLALKYL) AZOLE DERIVATIVES IN THE STRUCTURE OF OXIME ESTER

(71) Applicants: Suat Sari, Ankara (TR); Sevim Dalkara, Ankara (TR); Selma Sarac Tarhan, Ankara (TR); Arzu Karakurt, Malatya (TR)

(72) Inventors: Sevim Dalkara, Ankara (TR); Selma Sarac Tarhan, Ankara (TR); Arzu Karakurt, Malatya (TR)

(73) Assignee: Suat Sari, Ankara (TR)

( * ) Notice: Subject to any disclaimer, the term of this patent is extended or adjusted under 35 U.S.C. 154(b) by 0 days.

(21) Appl. No.: 15/022,723

(22) PCT Filed: Sep. 16, 2014

(86) PCT No.: PCT/TR2014/000343
§ 371 (c)(1),
(2) Date: Mar. 17, 2016

(87) PCT Pub. No.: WO2015/041620
PCT Pub. Date: Mar. 26, 2015

(65) Prior Publication Data
US 2016/0229817 A1    Aug. 11, 2016

(30) Foreign Application Priority Data

Sep. 19, 2013 (TR) .............................. a 2013/11057

(51) Int. Cl.
*C07D 233/61* (2006.01)
*C07D 249/08* (2006.01)

(52) U.S. Cl.
CPC ......... *C07D 249/08* (2013.01); *C07D 233/61* (2013.01)

(58) Field of Classification Search
None
See application file for complete search history.

(56) References Cited

PUBLICATIONS

Yang et al. (Jingxi Huagong, vol. 20, Issue 2, pp. 123-125, 128, 2003).*

* cited by examiner

*Primary Examiner* — Bong-Sook Baek
(74) *Attorney, Agent, or Firm* — Ladas & Parry LLP

(57) ABSTRACT

This invention is related to the antifungal compounds having azole structure in Formula (1), and hydrates, solvates, pharmaceutically acceptable salts or geometric isomers thereof. Formula (1).

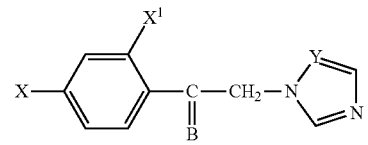

(1)

4 Claims, No Drawings

ANTIFUNGAL COMPOUNDS OF (ARYLALKYL) AZOLE DERIVATIVES IN THE STRUCTURE OF OXIME ESTER

FIELD OF THE INVENTION

This invention relates to antifungal compounds having azole structure. This invention is related to the compounds of Formula 1, geometric isomers or pharmaceutically acceptable salts thereof:

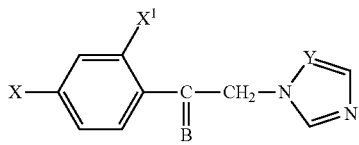

Formula 1 wherein

X is hydrogen, chlorine, fluorine, methyl, methoxy, nitro, phenyl;

$X^1$ is hydrogen or chlorine; and

Y is either carbon or nitrogen. B has the following structure:

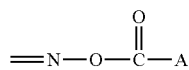

wherein A is selected from the group of alkyl, cycloalkyl, arylalkyl, or aryl compounds.

BACKGROUND OF THE INVENTION

Increase in the incidence of serious fungal infections is currently one of the most important problems of clinical medicine. Fungal infections may cause serious problems, even death, especially when the immune system is compromised like in the case of tuberculosis, cancer, AIDS, organ transplantation etc. Common use of medical devices such as prosthetic joints and coronary stents to improve life quality and increase lifespan is another recent cause for fungal infections. One of the major issues with antifungal chemotherapy is the development of resistance, which predisposes to "opportunistic" fungal infections whose cure is usually difficult and even impossible. *Candida* sp. are the prime culprit of hospital infections. *Candida albicans*, which normally is present in healthy individuals, is a crucial pathogen which causes invasive candidiasis in patients with immune-compromised conditions such as diabetes, cancer, AIDS and results in 30-40% mortality. Additionally, incidence of invasive candidiasis caused by non-*albicans Candida* sp. has increasingly been reported around the world in recent years. These species, which are less sensitive to main antifungal drugs, are *Candida albicans, Candida glabrata, Candida parapsilosis*, and *Candida crusei*.

Antifungal therapy for fungal infections is a long-lasting one and the recurrent rate is high. Moreover, antifungal medicaments have led to increase in toxicity due to the similarities between fungal and eukaryotic mammalian cells. Dose restriction due to the increased toxicity, on the other hand, lowers the chance of success. Accordingly, developing novel and more efficacious antifungal medicaments with a broad spectrum of action, systemic efficacy and lower side effects is an urgent and significant matter.

Imidazole-derivative antifungal drugs used since 1978 are wide-spectrum fungustatic agents. They are preferred for systemic fungal infections due to their lower toxicity. Together with triazole derivatives, which have the same antifungal spectrum with imidazole derivatives, they are called azole antifungals. Since more slowly metabolized, triazole derivatives possess a longer duration of action, milder direct toxicity, and no endocrine side effects. For these reasons, azole antifungals are superior to other antifungals and they are currently the most widely studied antifungal group.

The fact that certain fungus strains are resistant to currently available antifungals of the azole group in the market (econazole, miconazole, clotrimazole, ketoconazole and fluconazole) is another problem awaiting solution. In conclusion, developing new compounds with high antifungal activity, minimum drug interaction profile, low side effects and toxicity, effective against resistant strains and systemic use is an urgent matter of antifungal chemotherapy.

In addition to an azole group (imidazole, triazole), azole antifungal drugs involve at least one aromatic group in their structure which enhances the lipophilicity of the molecule. Some molecules contain an additional hydrophobic group in addition to that lipophilic aromatic group. They exhibit their activity by forming a coordination bond with "the iron ion of heme" in the active site of CYP51 enzyme via N3 nitrogen of imidazole ring or N4 nitrogen of triazole ring in the azole group.

Designing new azole antifungal compounds which are active against the resistant strains is an important subject for both medicinal chemists and clinicians especially due to the increase in infections caused by azole-resistant fungus strains.

Azole antifungals used today include groups such as alcohol, ether, oxime ether, and dioxolane as functional group on the alkyl chain that links between the lipophilic aryl group and the azole group. Therefore, using different functional groups into the linker chain is frequently applied in order to improve antifungal activity profiles of compounds. For instance, oxiconazole, which is used as an antifungal drug, has oxime ether structure as the linker chain functional group (Formula 2).

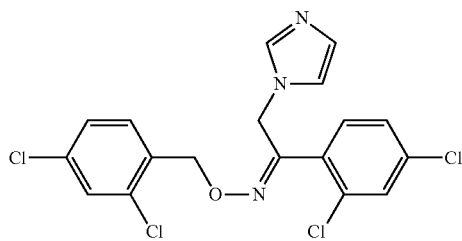

Formula 2

As 2-(1H-imidazol-1-yl)-1-naphthylethanone oxime ether/ester derivatives were found to possess antifungal activity along with 2-(1H-imidazol-1-yl)-1-phenyl/substituted phenyl/naphthyl ethanol ether/ester derivatives, scientists were encouraged to develop new derivatives by making modifications on these groups. Among these derivatives developed, alcohol and oxime ether and alcohol esters with phenyl and halo-substituted phenyl rings as aromatic group were found promising in terms of antifungal activity. Various carboxylic acid ester derivatives of 2-(1H-imidazol-1-yl)-1-phenyl/substituted phenylethanol, especially, were found to be effective at lower concentrations than fluconazole which is used as the standard compound and said compounds were also found to exhibit remarkable antifungal activity against certain resistant isolated strains.

SUMMARY OF THE INVENTION

The present invention is related to antifungal compounds having azole structure. This invention provides compounds having a structure illustrated in Formula 1 and hydrates, solvates, pharmaceutically acceptable salts or geometric isomers thereof:

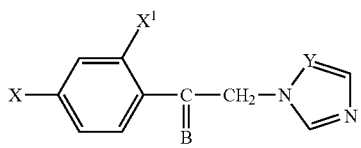

Formula 1 wherein
X=hydrogen, chlorine, fluorine, methyl, methoxy, nitro, phenyl,
$X^1$=hydrogen or chlorine, and
Y is selected as either a carbon or nitrogen.
B has the following structure:

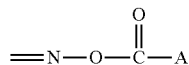

wherein A is selected from the group of alkyl, cycloalkyl, arylalkyl, or aryl compounds.

Object of the Invention

The object of this invention is to develop systemically effective novel compounds of (arylalkyl)azole structure, which are more potent, have fewer side effects, and better pharmacokinetic properties than clinically used other antifungal drugs, e.g. commercially available azole antifungal drugs, by means of introducing phenyl/substituted phenyl ring as lipophylic aryl group into the (arylalkyl)azole structure, and oxime ester structure into the linker chain.

DETAILED DESCRIPTION OF THE INVENTION

This invention relates to antifungal compounds having azole structure. This invention provides compounds having a structure illustrated in Formula 1, geometric isomers or pharmaceutically acceptable salts thereof:

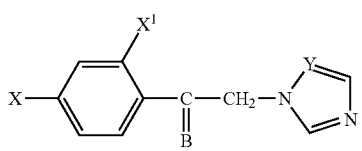

Formula 1 wherein
X=hydrogen, chlorine, fluorine, methyl, methoxy, nitro, phenyl,
$X^1$=hydrogen or chlorine, and
Y is either carbon or nitrogen. B has the following structure:

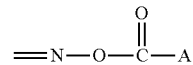

wherein A is selected from the group of alkyl, cycloalkyl, arylalkyl, or aryl compounds.

Due to the potential pharmacophore "oximino" group, oxime and oxime esters have a wide range of pharmacological activity spectrum. Oximino group usually is an activity modifier or occasionally responsible for the direct activity. The compounds of the present invention are potential antifungal compounds with respect to their chemical structure for treatment of fungal infections.

Compounds related to this invention are synthesized according to the following procedures.
Bromination of Acetophenone/Substituted Acetophenone (Formation of Phenacyl/Substituted Phenacyl Bromides)

Synthesis of 2-bromo-1-phenyl/1-(substituted phenyl)ethanone derivatives

The solution of 50 mmol acetophenone or substituted acetophenone in 50 ml acetic acid is stirred in ice bath and to this solution, three drops of hydrobromic acid is added. The solution of 50 mmol bromine diluted with 2.5 ml acetic acid was added drop wise to the reaction mixture while it is vigorously stirred. When the addition of bromine is completed, the reaction mixture is stirred for 2 hours at room temperature. The reaction mixture is poured in ice-water; the precipitate taken by filtration, is washed with sodium bicarbonate solution and dried in darkness. It is purified via crystallization from methanol/water mixture.
N-Alkylation of Imidazole or Triazole Synthesis of 2-(1H-imidazol-1-yl/1H-1,2,4-triazol-1-yl)-1-phenyl/1-(substituted phenyl) ethanone derivatives The solution of 10 mmol phenacyl bromide or substituted phenacyl bromide derivative in 2.5 ml dimethylformamide is slowly added to the solution of 30 mmol imidazole or triazole in 2.5 ml dimethylformamide (DMF) cooled in ice-bath. It is stirred for 2 hours in ice-bath then overnight at room temperature. Afterwards, it is poured in ice-water, the resulting precipitate is filtered, dried, and purified via crystallization.

Synthesis of 2-(1H-imidazol-1-yl/1H-1,2,4-triazol-1-yl)-1-phenyl/1-(substituted phenyl) ethanone oxime 0.015 mmol 2-(1H-imidazol-1-yl/1H-1,2,4-triazol-1-yl)-1-phenyl/1-(substituted phenyl) ethanone and 0.03 mol hydroxylamine hydrochloride are dissolved in 75 ml ethanol and alkalinized with the solution of 15 N sodium hydroxide to pH 11. The mixture is then heated under reflux for 3 hours. The resulting precipitate is filtered off and the filtrate is evaporated to dryness. The residual is dissolved in water and acidified with saturated hydrochloric acid to pH 5. The precipitate, which is taken by filtration, is purified via crystallization by methanol.

Synthesis of oxime ester derivatives

The suspension or solution of the proper carboxylic acid (2.5 mmol) and 2-(1H-imidazol-1-yl/1H-1,2,4-triazol-1-yl)-1-phenyl/1-(substituted phenyl)ethanone oxime (2.5 mmol) in dry dichloromethane is stirred at 00° C. under gaseous nitrogen. To this mixture, the solution of N,N'-dicyclohexylcarbodiimide (2.5 mmol) and 4-dimethylaminopyridine (0.17 mmol) in dry dichloromethane is slowly added. The mixture is stirred at room temperature or at a proper temperature. The compounds are purified by appropriate methods.

Isolation and purification steps of the compounds, separation of their E and Z isomers, and isolation of these isomers are the critical steps.

As an embodiment of this invention, the synthesis of 2-(1H-imidazol-1-yl)-1-phenylethanone O-cinnamoyl oxime, one of the compounds of the invention, is given along with the synthesis of its starting materials:

Synthesis of 2-bromo-1-phenylethanone

The solution of 50 mmol acetophenone in 50 ml acetic acid is stirred in ice bath and three drops of hydrobromic acid is added. To the reaction mixture, the solution of 50 mmol bromine diluted in 2.5 ml acetic acid was added drop wise while the reaction medium is vigorously stirred. When the addition of bromine solution is completed, the reaction mixture is stirred for 2 hours at room temperature. Then the reaction mixture is poured in ice-water. The precipitate, which is taken by filtration, is washed with sodium bicarbonate solution and dried in darkness. It is purified via crystallization from methanol/water mixture (melting point: 46° C., yield: 75%).

Synthesis of 2-(1H-imidazol-1-yl)-1-phenylethanone

To the solution of 30 mmol imidazole in 2.5 ml DMF cooled in ice-bath, the solution of 10 mmol 2-bromo-1-phenylethanone in 2.5 ml DMF is added slowly. It is stirred for 2 hours in ice-bath then overnight at room temperature. Afterwards, it is poured in ice-water and the resulting precipitate is filtered, dried, and purified via crystallization from ethyl acetate/n-hexane (melting point: 109-10° C., yield: 70%).

Synthesis of 2-(1H-imidazol-1-yl)-1-phenylethanone oxime 2-(1H-imidazol-1-yl)-1-phenylethanone (15 mmol) and hydroxylamine hydrochloride (30 mmol) are dissolved in 75 ml ethanol and the pH of this solution is adjusted to 14 with 15 N aqueous sodium hydroxide. The mixture is heated under reflux for 3 hours, ethanol is evaporated under vacuum. The residue is dissolved in water and the derivative is acidified with the solution of hydrochloric acid. The compound precipitates at the point of pH 5. The precipitate is taken by filtration and purified via crystallization with methanol (melting point: 166° C., yield: 57%).

Synthesis of 2-(1H-imidazol-1-yl)-1-phenylethanone O-cinnamoyl oxime

Suspension of 2-(1H-imidazol-1-yl)-1-phenylethanone oxime (1 mmol) in dry dichloromethane is stirred under room temperature. To this mixture, trans-cinnamic acid (2 mmol), the solution of dicyclohexylcarbodiimide (2 mmol) and dimethylaminopyridine (0.17 mmol) in dry dichloromethane are added. The reaction mixture is stirred at room temperature for 6-12 hours. Precipitating dicyclohexylurea is filtered off and following this, dichloromethane is removed by evaporation under vacuum. The residue is purified via column chromatography and crystallized from ethyl acetate/n-hexane (melting point: 136-138° C., yield: 30%).

The invention claimed is:

1. A compound of the following formula

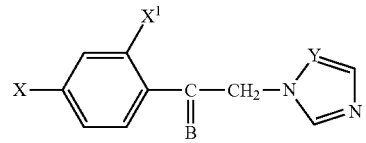

wherein,

X is hydrogen, chlorine, fluorine, methyl, methoxy, nitro, or phenyl,

X is hydrogen or chlorine, and

Y is carbon and B has the following structure:

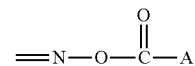

and wherein A is alkyl, cycloalkyl, arylalkyl, or aryl group;

or a hydrate, solvate, pharmaceutically acceptable salt, or geometric isomer thereof.

2. A pharmaceutical formulation comprising a compound according to claim 1 as active ingredient and at least one pharmaceutically acceptable excipient.

3. A method for treating a fungal infection comprising administering a compound according to claim 1 to a subject in need thereof.

4. A method for treating a fungal infection comprising administering a composition according to claim 2 to a subject in need thereof.

* * * * *